US00RE35263E

United States Patent [19]

Silva et al.

[11] E Patent Number: Re. 35,263

[45] Reissued Date of Patent: Jun. 4, 1996

[54] METHOD AND APPARATUS FOR FABRICATING DENTAL MODELS

[75] Inventors: Deborah Silva, Ferndale, Calif.; Robert G. Lowry, Highlands Ranch; Robert Silva, Lakewood, both of Colo.

[73] Assignee: The Silva Group, Inc., Lakewood, Colo.

[21] Appl. No.: 147,349

[22] Filed: Oct. 27, 1993

Related U.S. Patent Documents

Reissue of:

[64] Patent No.: 5,197,874
Issued: Mar. 30, 1993
Appl. No.: 901,203
Filed: Jun. 19, 1992

[51] Int. Cl.[6] ..... A61C 19/00

[52] U.S. Cl. ..... 433/74; 433/34

[58] Field of Search ..... 433/34, 35, 36, 433/60, 74, 213

[56] References Cited

U.S. PATENT DOCUMENTS

| | | | |
|---|---|---|---|
| 2,629,929 | 3/1953 | Levine et al. . | |
| 3,937,773 | 2/1976 | Huffman | 264/17 |
| 4,122,606 | 10/1978 | Roman . | |
| 4,368,042 | 1/1983 | Felstead et al. | 433/213 |
| 4,371,339 | 2/1983 | Zeiser | 433/74 |
| 4,398,884 | 8/1983 | Huffman | 433/74 |
| 4,439,151 | 3/1984 | Whelan | 433/60 |
| 4,459,110 | 7/1984 | Jackson | 433/74 |
| 4,462,801 | 7/1984 | Lagios | 433/60 |
| 4,538,987 | 9/1985 | Weissman | 433/60 |
| 4,600,385 | 7/1986 | Lee | 433/60 |
| 4,608,016 | 8/1986 | Zeiser | 433/74 |
| 4,721,464 | 1/1988 | Roden et al. | 433/74 |
| 4,767,330 | 8/1988 | Burger | 433/213 |
| 4,767,331 | 8/1988 | Hoe | 433/213 |
| 5,087,197 | 2/1992 | Sullivan | 433/74 |

FOREIGN PATENT DOCUMENTS

| | | | |
|---|---|---|---|
| 2922045 | 12/1980 | Germany | 433/60 |
| 2923208 | 12/1980 | Germany | 433/60 |
| 3315870 | 11/1984 | Germany | 433/213 |
| WO88/10101 | 12/1988 | Germany . | |

*Primary Examiner*—Nicholas D. Lucchesi
*Attorney, Agent, or Firm*—Gary M. Polumbus; Holland & Hart

[57] ABSTRACT

Disclosed is a base plate assembly for use in mounting a die-stone dental replica, the assembly including a base plate that has a configuration commensurate with at least one dental quadrant, and having a planar upper surface characterized by an array of transverse elongate rectangular sockets. A plurality of mounting blocks are assembled in side-by-side relationship along the plate planar surface, each block having a downward projection adapted to frictionally and releasably hold the block on the base plate, and extending from the tops of the blocks are anchoring tabs designed to be embedded in the wet positive mold of a dental impression and affixed therein when the mold material cures. In a preferred embodiment, the base plate has a modular configuration and is interconnectable with an identical modular unit to form a combined base plate having a configuration commensurate with full bilateral upper or lower dental quadrants.

36 Claims, 3 Drawing Sheets

METHOD AND APPARATUS FOR FABRICATING DENTAL MODELS

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to dental replicas and, more particularly, to a method for mounting dental replicas and to a base plate assembly for mounting replicas.

2. Description of the Prior Art

When a dentist determines that a patient requires a crown, bridge, inlay or other common dental prostheses, it is necessary that the dentist first obtain a negative impression of the patient's teeth and gums, including the negative impression of the dental quadrant or quadrants containing the affected teeth. Dental impressions may be unilateral, bilateral, upper or lower, etc. depending on the work to be done. This is customarily accomplished by having the patient bite into a mass of yieldable, rubber-like impression material carried on a holder so that a mold cavity of teeth and associated gums is created. The material will cure in a short time and retain an exact impression of the patient's teeth and gums. This negative impression will then be sent to a dental technician who will use it in any of a variety of conventional techniques to arrive at a stone cast dental replica. The cast replica is mounted in such a way to allow individual replicas of affected teeth, such as the tooth needing a crown or cap, to be segregated from the greater replica. This individual segment is ordinarily removed and repositioned into the greater model several times as work progresses to ensure that the end product being fashioned has proper alignment and visual conformity with the greater model.

Preparation of the negative dental impression is a well known preliminary step, however there are a variety of techniques and devices employed by the dental technician in processing the negative dental impression into a stone cast replica that is mounted in a fashion suitable for work on the individual removable dental segments. Unfortunately, none of the conventional and prior art methods and devices are without limitations and drawbacks. For example, several well established prior art techniques require two pourings of mold material, one for the die stone replica of the teeth and gums, and another for the formation of the base upon which the replica is attached. Oftentimes the base of the replica must undergo grinding to from a flat surface in which drill hole locations must be located and marked. Special drilling equipment is then used to drill holes, and dowel pins are then selected and mounted in the holes by use of adhesive. In many cases sleeves are applied to the mounted pins and the sleeved pins inserted into the uncured base which dries to retain the embedded sleeves. Such techniques are inevitably tedious and time consumptive, as well as consumptive of materials and supplies. It is also noted that the special electrically powered equipment represents an appreciable cost outlay. Additionally, special training and skill of the technician must be relied on in order to properly implement such techniques.

U.S. Pat. No. 4,122,606 is an example of a two-pour system that involves the drilling of holes and the use of dowel pins, etc. U.S. Pat. Nos. 4,767,330, 4,398,884 and 3,937,773 purport to bring certain improvements to the industry. Nevertheless, each of these disclosures requires the steps of making two molds and bring associated costs in labor, material, supplies and time. It is also noted in these prior art techniques that a die stone surface of a removable tooth segment must be brought into engagement with another stone cast surface or with a rigid plastic surface every time the segment is replaced in the greater replica. This can lead to an abrasion of the die stone and a loss in the integrity of the fit.

The prior art also includes some one-pour techniques that avoid some of the aforestated drawbacks. For example, U.S. Pat. Nos. 4,371,339, 4,368,042 and 4,721,464. It is noted, however, that U.S. Pat. No. 4,721,464 involves the positioning and aligning of individual dowel pins and guides, and die stone surfaces must be brought against hard plastic surfaces. U.S. Pat. No. 4,371,339, even though it employs a special base element for releasably supporting its dental replica, nevertheless involves the tedious and skill-required task of locating pin hole locations and drilling holes in which pins must be mounted using adhesives, heat or pressure. While U.S. Pat. No. 4,368,042 does not require two pours, it does require the use of two jaw-shaped plates, pre-molded of rigid plastic or the like. One of the plastic plates must be sawed through when an individual tooth is to be segregated.

It is also noted that the prior art is replete with various devices useful in the formation and mounting of a dental replica, but they invariably appear to be complex and costly.

SUMMARY OF THE INVENTION

In view of the foregoing shortcomings and limitations of prior techniques and apparatus, it is a general object of the invention to provide an apparatus and a technique by which the dental technician can mount a working model of a dental replica in a manner that is expeditious, accurate and reliable, yet economical in time and materials.

Another, more particular object is to provide a technique and apparatus by which a minimum of steps is required to produce and mount a dental replica with removable segments.

A further object is to provide a method for mounting a dental replica which can be successfully carried out without an undue amount of special training and skill of the technician.

Yet another object of the invention is to provide for the production and mounting of a dental replica that does not require dowel pins, hole drilling, grinding of surfaces and special adhesives.

Yet a further object is to provide means that allow individual tooth segments to be repeatedly removed and replaced to the greater replica with deterioration of mating and interlocking surfaces.

A still further object of the present invention is to employ a modular mounting plate for a dental replica, which modular plate can be used singly to support any selected dental quadrant, or connected to another identical modular piece to provide a base for a full upper or lower bilateral replica.

Yet a further object is to provide such a modular base plate in a method that does not require it to be sawed through in order to construct an individual dental segment replica.

These and additional objects and advantages are provided by the present invention of a one-pour method for making and mounting a stone cast replica of a patient's teeth and gums. The improved method features providing a base plate assembly that includes a base plate having a configuration commensurate with a least one quadrant of a person's dental structure and including a flange that has a planar upper surface characterized by an arrangement of a plurality of elongate transverse sockets spaced therealong.

The base plate assembly further includes a plurality of mounting blocks that are releasably securable to the flange planar surface. Each block has opposed side walls, a top and a bottom, the bottom designed to engage the upper planar surface for vertical support, and from the bottom there is a downward projection designed to be frictionally and releasably received in a corresponding one of the sockets, to stabilize the blocks in side-by-side relationship along the flange upper planar surface. Each block has an anchoring tab extending upwardly from its top.

The improved one-pour method of the invention includes filling a negative dental impression with uncured pourable dental casting stone, inverting the base plate assembly and immersing the anchoring tabs of the blocks within the wet stone material, and then allowing the material to harden so as to fixedly secure the tabs within the hardened material. The dental impression mold is then removed from the cured stone to provide a dental replica attached to the novel base assembly. Individual, removable dental segments may then be provided by making vertical saw cuts through the die stone replica, each cut extending to upper edges of at least one block to provide a removable model segment that comprises a selected tooth and gum replica affixed to at least one of the blocks.

In a preferred embodiment of the base plate assembly, the base plate has a modular structure with advantages of versatility and economy that will become evident, and the base plate includes a support core having a main generally straight interconnecting side and an arcuate side from which extends a flange which provides the aforementioned upper planar surface for supporting the mounting blocks of the invention. Additionally in this preferred modular embodiment the support core provides an arcuate wall that adjoins the planar surface and which arcuate wall is adapted for attachment to an articulator, a hinged device used throughout the industry for simulating jaw movement. The symmetry of the modular plate is such that the flange has a lower side that is the mirror image of the upper side of the plate with respect to a planar surface for supporting mounting blocks and an arcuate wall. A further feature of the preferred embodiment is the provision of androgynous connecting means on the main side of the support core by which one modular unit can be connected to another identical modular unit to provide a plate having a curvature commensurate with that of two adjoining bilateral dental quadrants. Additionally, it is noted that the sockets preferably have a generally rectangular transverse cross-sectional configuration and that each downward projection has an upper portion shaped to snugly fit the upper part of a socket to hold the block against lateral movement and has a lower portion with lateral protuberances that frictionally engage the socket walls to hold the block against unwanted outward movement, particularly when the base plate is inverted. The protuberances are spaced on opposite sides of the downward projection such that their engagement with the socket causes the downward projection to resiliently bow about a vertical axis through the downward projection.

The accompanying drawings illustrate the invention with more clarity and particularity, and together with the detailed description serves to explain the principles of the invention.

DETAILED DESCRIPTION OF THE INVENTION

Figure 1:
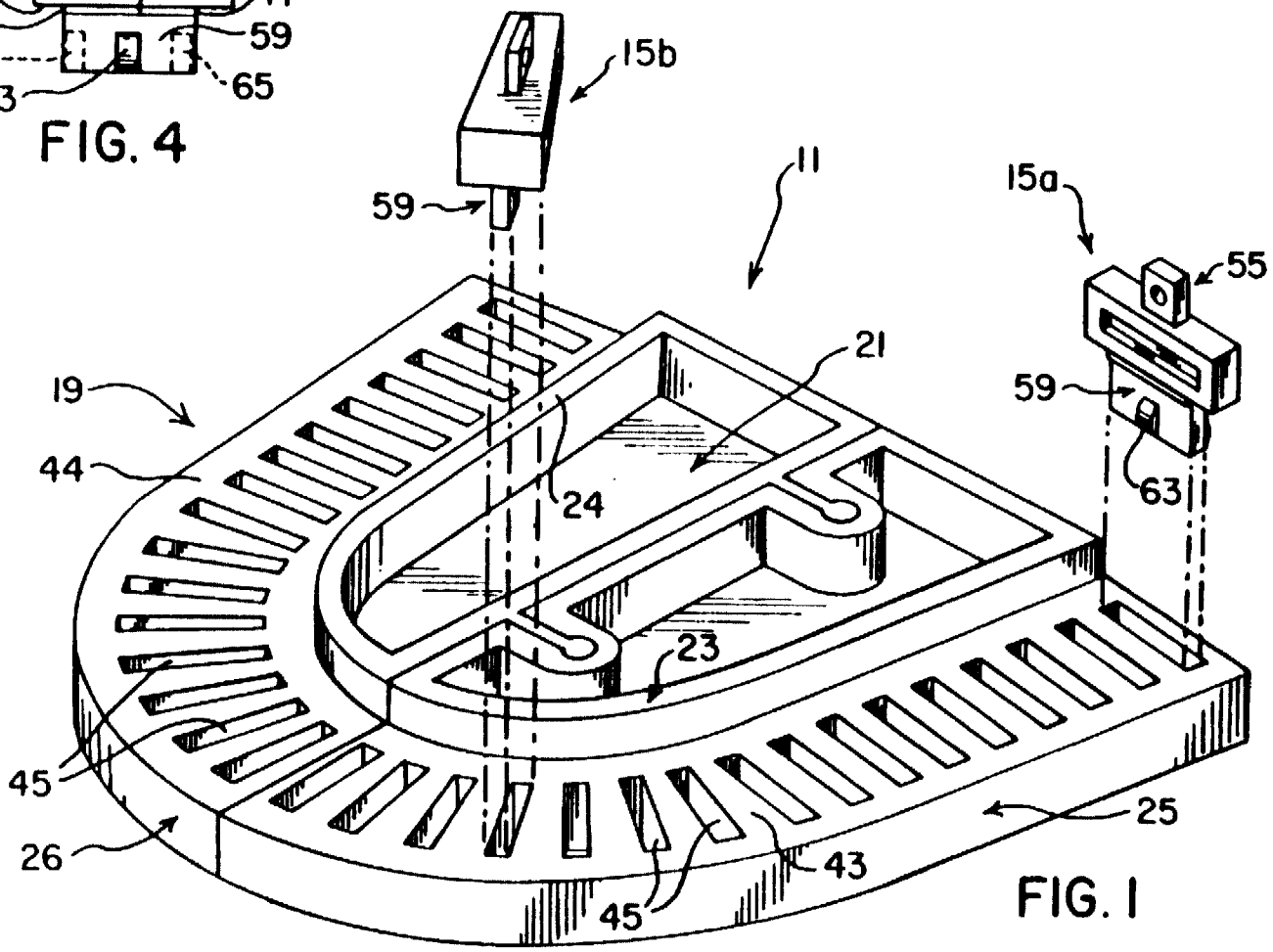
FIG. 1 is an exploded perspective view of a preferred embodiment of a base plate assembly according to the present invention, and employed in the process of the invention for forming a working dental model.

Referring now to the drawings, FIG. 1 shows a preferred embodiment of a base plate assembly according to the present invention, which assembly will be seen to be advantageously employed in an improved method for mounting a dental replica. The base plate assembly 11 is seen to comprise at least a first base plate 13a and a number of mounting blocks including exemplary blocks 15a and 15b which are adapted to be releasably mounted upon the base plate in a manner to be described. These components of the invention are constructed of a suitable dense polymeric material, such as ABS or styrene plastic for example, according to techniques well known in the plastics molding industry. These components can also be fashioned of various other suitable materials including certain composite materials, and metals such as aluminum.

Figure 2:
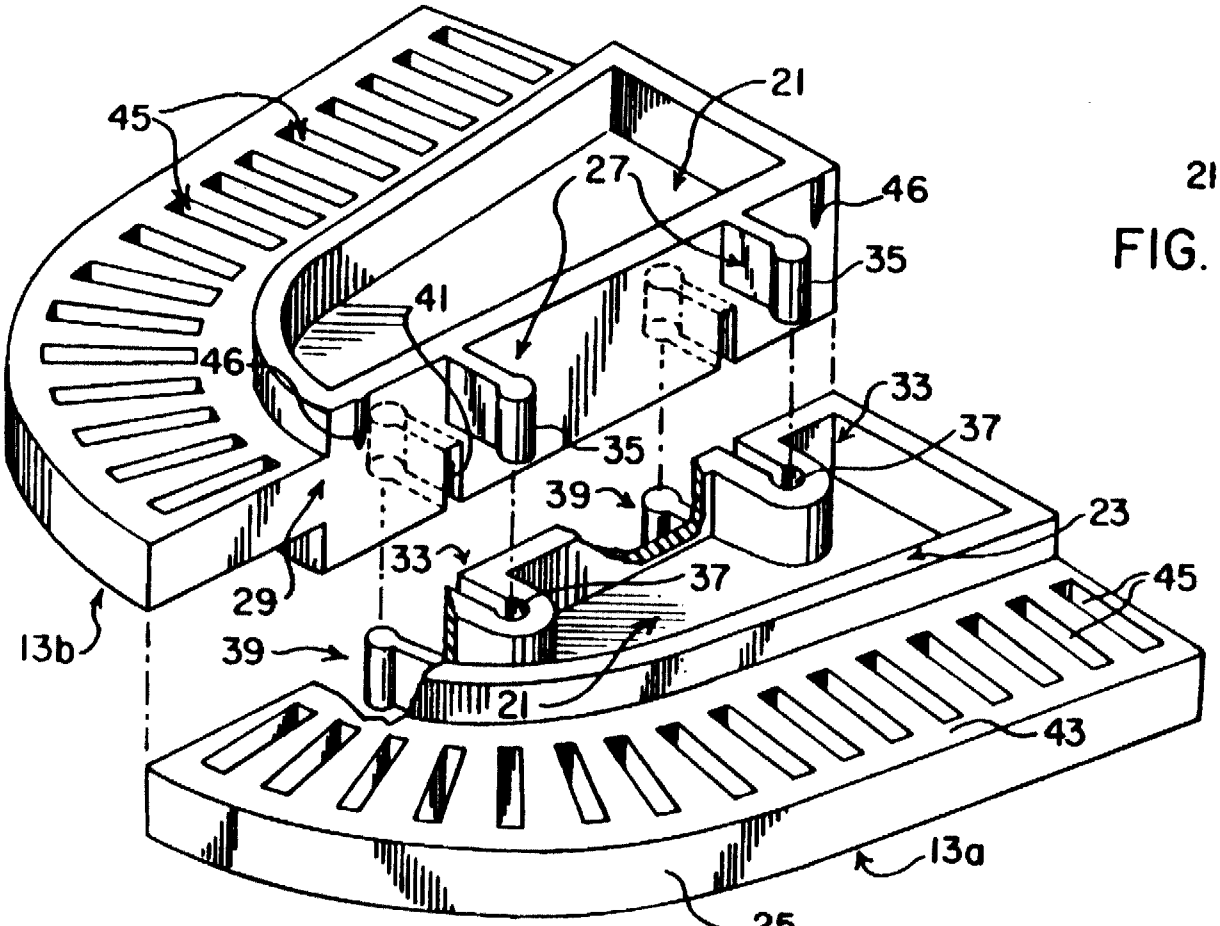
FIG. 2 is an exploded perspective view illustrating the use of a modular base plate according to the present invention.
Figure 8:
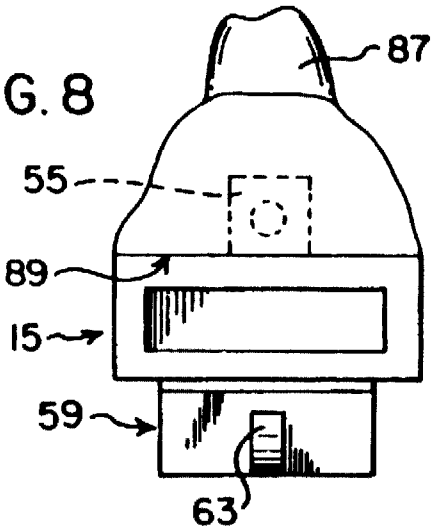
FIG. 8 is a side elevational view of a removable and replaceable dental replica segment under the present invention.

It is noted that plate 13a is preferably provided with a unique structure that allows it to function as a modular unit with, among other things, advantages of economy and versatility, and is structured such that as best shown in FIG. 2, a second unit 13b, identical to unit 13a, can be easily attached to unit 13a to form a generally U-shaped combined base plate 19, shown in FIG. 1. A closer look at FIG. 2 shows that base plate module 13b includes a core portion 21, an arcuate wall member 23, a flange 25 that extends from wall member 23, a set of male locking tabs 27 that project from the upper part of wall 29, and a pair of female locking slots 41, within the lower part of wall 29. Note that what is known in the plastics industry as"crush ribs," are provided on wall 29 as indicated by reference numeral 46. As suggested by FIG. 2, a first modular plate 13b can be attached to a second modular plate 13a by aligning the two plates such that the cylindrical ends 35 of the male locking tabs 27 are moved vertically into frictional attachment with the cylindrical cavities 37 of the modular plate 13a. It will be appreciated that at the same time, the male locking tabs 39 of modular plate 13a will be frictionally received in corresponding slots 41 in the modular piece 13b. The "crush ribs" 46 of one plate will frictionally engage the wall 29 of the other plate during the connection process. This operation will quickly and firmly secure the two modular pieces together to form the combined base plate 19 shown in FIG. 1.

As shown in FIG. 1, in the combined base plate 19 wall members 23 and 24 combine to form a generally U-shaped configuration and the upper planar surfaces 43 and 44 of flanges 25 and 26 respectively also combine in a generally U-shaped configuration. It is to be noted that the bottom side of a base plate 13a is a mirror image of its upper side with respect to its planar surface and arcuate wall member. It will be later appreciated that the combined wall members 23 and 24 advantageously provide a generally U-shaped top platform to which any suitable adhesive such as hot melt adhesive can be applied to attach a combined base plate assembly to an articulator device. In some cases, as dictated by the articulator design, the wall members 23 and 24 can be adapted for being attached to the articulator using threaded fasteners. An array of rectangular through-slots 45 are provided in the flange 25 of each modular base plate.

The base plate assembly 11 as aforementioned also features a number of mounting blocks 15a that have a rectangular configuration in plan view and that are attachable to the straighter portions of the surfaces 43 and 44. The blocks 15b have a generally wedge-shaped configuration and are designed to be attached along the curved portions of the plate planar surfaces.

Figure 4:
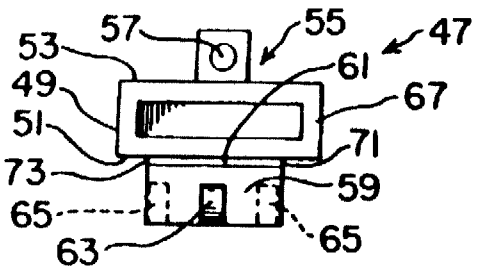
FIG. 4 is a side elevational view of a mounting block according to the present invention.
Figure 3:
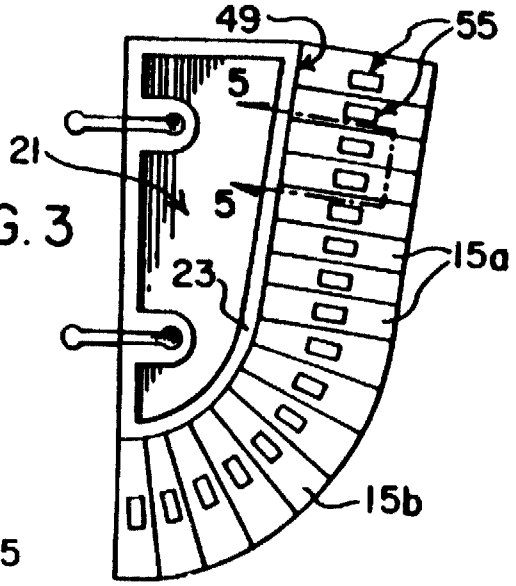
FIG. 3 is a top plan view of a base plate assembly with blocks mounted, according to the present invention.

FIG. 4 shows that a representative mounting block 47 includes a rear wall 49, a bottom 51, and a top wall 53. A generally rectangular anchor tab 55 extends from the top wall 53 and is provided with an aperture 57. The downward projection 59 has a rectangular seat 61 in its upper portion, and a single protuberance 63 on one side and two protuberances 65 projecting from the other side. The downward projections 59 of mounting blocks 15a and 15b are designed to be received in the slots 45 such that a full array of blocks 15a and 15b are releasably secured to the flange 25 in side-by-side relationship as best illustrated in FIG. 3, with the rear walls 49 of the blocks abutting the outer face of wall members 23.

Figure 9:
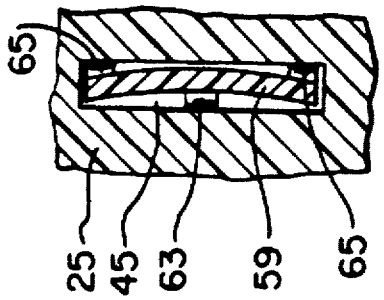
FIG. 9 is a sectional view taken along the line 9—9 of FIG. 5.
Figure 5:
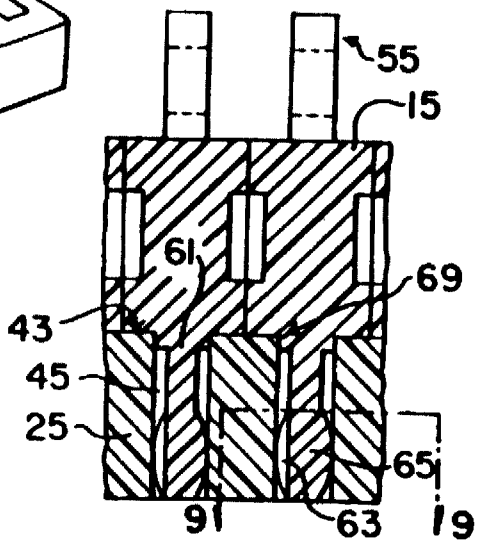
FIG. 5 is an enlarged sectional view taken along the line 5—5 of FIG. 3.

FIG. 5 best shows how mounting blocks 15 will engage the upper flange surface 43 and the inner walls of slots 45 in a manner that firmly supports the blocks in an upright orientation in which they are stabilized against lateral movement or tilting, and holds them against vertical outward movement. More particularly, FIG. 5 shows how the flat bottom surface of a block 15 is supported against the flat flange surface 43, and how the vertical side walls 69 of seat portion 61 snugly engage the upper walls of slot 45. The front and rear walls 71 and 73 respective, of the seat portion, shown in FIG. 4, will snugly engage front and rear walls (not shown) of slot 45. FIG. 5 also shows how the protuberances 63 and 65 engage the sides of slot 45 to frictionally yet releasably bind a block in place. The two protuberances 65 and the single protuberance 63 will engage the walls of slot 45 in the fashion of an interference fit and will resiliently bow the downward projection 59 as shown in exaggerated fashion in FIG. 9 to provide the spring force which urges the protuberances into frictional engagement with the slot walls. It will be seen that the resulting holding force will hold the blocks in place for normal use of the base plate assembly, yet will allow a given block to be removed by hand when required. The protuberances have inclined upper and lower surfaces to ensure easy insertion and removal from a slot 45. Since the invention requires mutual engagement of plastic surfaces rather than surfaces that can be abraded, proper seating and alignment of blocks upon the base plate will be maintained in spite of repeated removals and replacements. Since the slots 45 pass completely through the flange, any required cleaning of them is facilitated. This also provides access to the bottoms of the downward projections of the blocks to allow pushing on the bottoms to assist removal of a block should it be necessary.

The aforedescribed mounting plate assembly can be employed in an improved one-pour method for making a dental replica and for mounting it in a fashion useful to the dental technician. The method is performed in the following matter. First, a denture impression (negative mold) is made of the patient's teeth and gums in a well-known manner and is supported on an impression holder 75 as illustrated in FIG. 6.

If it is desired to mount a replica of the entire upper quadrants or lower quadrants of the patient's teeth and gums, two of the invention's modular base plates are readily connected to form a combined base plate 19, supporting a full array of mounting blocks 15 in inverted fashion.

Figure 6:
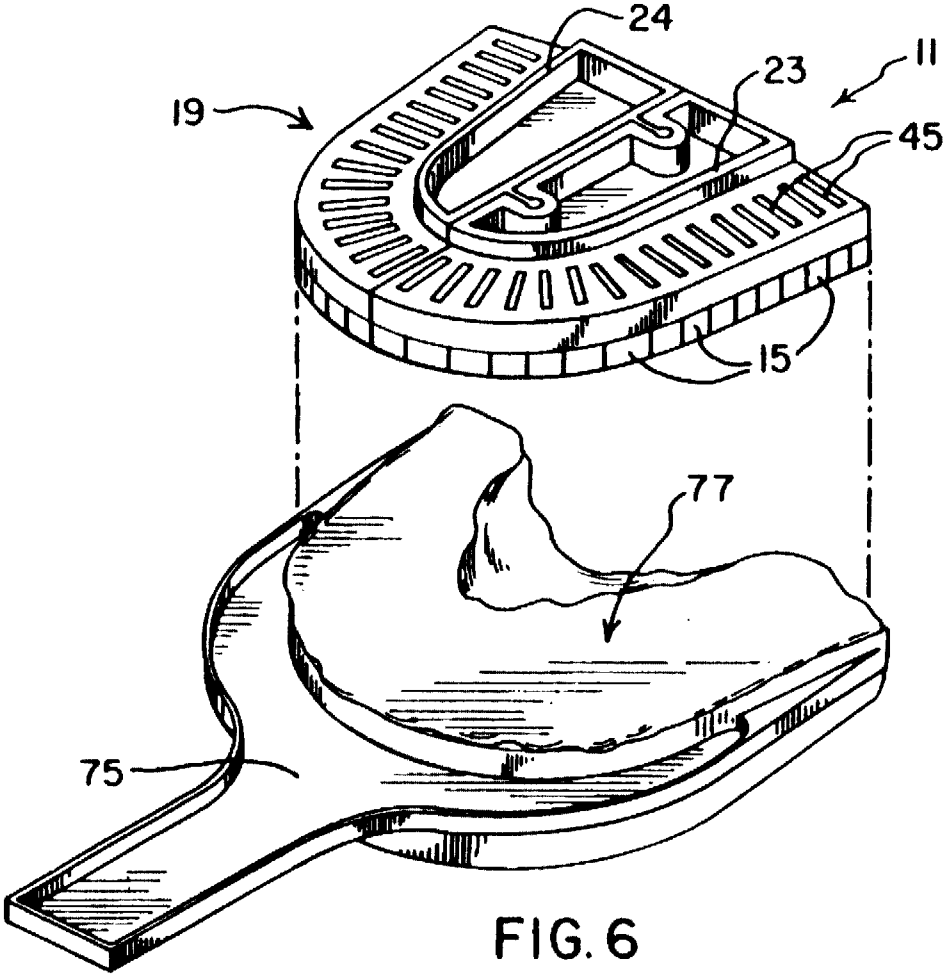
FIG. 6 is an exploded perspective view illustrating the use of the inventive mounting plate assembly in a method according to the present invention.

The denture impression carried on holder 75 is filled with a pourable form of a suitable die cast material which is shaped into a generally level surface 77 shown in FIG. 6. The process proceeds by aligning the base plate assembly 11 by hand with the U-shaped surface 77 of the wet die stone. The anchor tabs 55 may be pretreated by having small quantities of wet die stone applied thereto, using a spreader or the like. Next the assembly 11 is pressed downwardly into the surface 77 of the die stone, the anchor tabs 55 being completely immersed and the upper surfaces 53 of the mounting blocks being pressed into engagement with surface 77. Following the usual die stone curing period the somewhat rubber-like impression mold can be easily peeled away from the hardened stone to provide a stone-cast dental replica mounted upon base plate assembly 11. A neater, more aesthetically pleasing model can result if excess die stone gum mold is trimmed away using customary techniques so that the bottom edges of the molded gum will align with the curvature of the base plate. An example of the resulting structure is illustrated in FIG. 7 which shows the stone-cast denture replica 83 mounted according to the invention.

Figure 7:
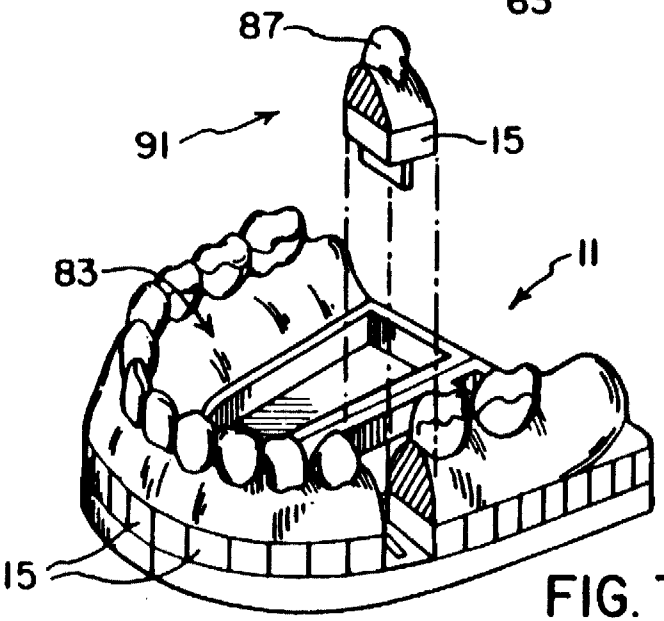
FIG. 7 is exploded perspective view of a dental replica mounted according to the present invention.

Finally, in order to segregate a particular stone denture segment, such as for example a segment 91 shown in FIG. 7 containing the replica of a tooth stub 87, two generally vertical saw cuts are made through the die stone to terminate at the upper edges of a selected block. In order to mount a relatively wide dental segment, two adjacent blocks may be used. Thus a selected stone replica segment is firmly affixed atop at least one block, and the segregated unit, such as individual replica 91 in FIG. 7, may be readily disengaged from its base plate and repeatedly removed and replaced as required during subsequent processing by the dental lab technician using known techniques. If it is necessary to mount the above working replica to an articulator, then this can be conveniently accomplished as described above. It should be evident that a single modular unit rather than the combined unit shown in FIG. 7 will be advantageously employed when only one denture quadrant is to be replicated. It will also be evident, because of the bilateral symmetry of a modular unit, that a modular unit will serve for either upper or lower quadrant replicas.

While particular embodiments of the invention have been described, it is not intended that the invention be limited thereto. Various modifications and variations may readily occur to those of ordinary skill in the art without departing from the true scope and breadth of the invention as defined in the claims which follow.

What is claimed is:

1. Apparatus for use in making a dental replica, comprising:

a) base plate having a plan-form configuration commensurate with at least one quadrant of a person's dental structure, said base plate including a flange portion having an arcuate planar upper surface with a plurality of transverse, elongate sockets arranged therealong in spaced-apart relationship; and b) a plurality of mounting blocks releasably attached to said flange upper surface, each said block having a planar lower surface adapted to engage said flange upper surface, and a downward projection adapted to make releasable friction engagement within a corresponding one of said sockets, and an anchor tab projecting upwardly from the top of each said block.

2. Apparatus as defined in claim 1 wherein said base plate and blocks are constructed of a dense polymeric material.

3. Apparatus as defined in claim 1 wherein said sockets comprise slots that extend vertically through said flange portion and wherein said flange portion has a lower side with a planar surface that is a mirror image of said flange upper planar surface.

4. Apparatus as defined in claim 3 wherein said base plate has an arcuate upright wall adjoining said flange upper planar surface, and said upright wall having a top surface adapted for attachment to an articulator.

5. Apparatus as defined in claim 1 wherein said blocks are generally rectangular in shape.

6. Apparatus as defined in claim 1 wherein each said socket has a generally rectangular transverse cross section and wherein said downward projection of each said block includes a rectangular upper part that is snugly receivable within said corresponding socket to hold its block against lateral and rotational movement and said downward projection having a lower portion with lateral protuberances for frictionally engaging said corresponding socket to hold to block against outward movement.

7. Apparatus as defined in claim 6 wherein said downward projection lower portion has first and second oppositely disposed major walls, and wherein there is a first protuberance on the middle of said first wall and said protuberances spaced apart at opposite ends of said second major wall.

8. Apparatus as defined in claim 7 wherein said protuberances make an interference fit within said socket and wherein said protuberances have sloped lower surfaces and are adapted to make sliding camming engagement with said socket as said downward projection is inserted in said socket.

9. Apparatus as defined in claim 7 wherein said downward projection is resiliently bowable about a vertical axis through said downward projection by virtue of said frictional engagement of said protuberances in said socket.

10. Apparatus as defined in claim 1 wherein each said anchor tab has a transversely extending sunken portion therein.

11. Modular base plate assembly for use in mounting a dental replica, including:

a) modular base plate having a configuration commensurate with a single quadrant of a person's dental structure and including a support core that has an interconnecting side and an arcuate side from which extends a flange portion, said flange portion having an upper planar surface and a planar lower surface, said flange portion characterized by a plurality of transverse, elongate through-slots arranged in spaced-apart relationship along said flange upper planar surface and said flange lower planar surface being a mirror image of said upper flange planar surface; and connecting means on the interconnecting side of said support core, which means is engagable with connecting means of a second modular base plate to secure two said base plates together to form combined plates having a general U-shaped configuration; and b) plurality of mounting blocks releasably mountable on said flange upper planar surface or lower planar surface, each said block having a front wall, rear wall, opposed side walls, top, and bottom, and a downward projection from said bottom, said projection adapted to make releasable holding engagement within a one of said through-slots, and each said block having an anchoring tab extending upwardly from said block top.

12. Modular base plate assembly as defined in claim 11 wherein said interconnecting side of said core has an upper and a lower part, and said connecting means comprises a male locking structure extending from said side upper part and a female locking structure in said side lower part.

13. Modular base plate assembly as defined in claim 11 wherein each said through-slot has an elongated, generally rectangular cross-sectional configuration.

14. Modular base plate assembly as defined in claim 13 wherein said downward projection has an upper part that snugly fits the upper region of its respective through-slot to hold said block against lateral and rotational movement, and the lower part of said downward projection is adapted to make frictional engagement within said through-slot to hold said block against upward movement.

15. Modular base plate as defined in claim 11 wherein said lower part of said downward projection has laterally extending protuberances for frictionally engaging opposed walls of said through-slots.

16. Modular base plate as defined in claim 11 wherein each said tab is generally rectangular and has a transversely extending indentation.

17. Modular base plate as defined in claim 11 wherein said support core has an upwardly extending ridge adjoining said upper planar surface, which ridge is adapted for attachment to an articulator.

18. Method for making a dental replica with at least one cast replica segment that is selectively detachable and replaceable with respect to said dental replica, including the steps of:

a) providing a base plate assembly that includes a base plate having a plan-form configuration commensurate with at least one quadrant of a person's dental structure, said base plate having an upper portion that includes a planar upper surface with a plurality of elongate, transverse, vertically extending sockets arranged therealong in spaced-apart relationship, and a plurality of mounting blocks, each block having an upper and a lower planar surface and a pair of opposed top side edges, said block lower surface engaging said base plate upper surface to support said block thereon, and a generally rectangular downward projection from the lower surface of said block adapted to make releasable frictional engagement within a corresponding one of said sockets, to support said block against rotational and lateral movement relative to said base plate, and an anchor tab projecting upwardly from the top of said block;

b) filling a dental impression mold with uncured dental casting material;

c) inverting said base plate assembly and immersing said block anchor tabs within said uncured casting material;

d) allowing said material to harden whereby said tabs are fixedly secured within said hardened material;

e) removing said dental impression mold from said hardened material to provide a dental replica of hardened material attached to said blocks mounted on said base plate; and f) making vertical cuts downwardly through said dental replica to top side edges of at least one of said blocks to provide a removable model segment comprising a selected tooth and gum replica affixed to at least one of said blocks.

19. Method as defined in claim 18 including the step of smearing a quantity of said uncured material over said anchor tabs prior to immersing said tabs in said uncured material.

20. Method as defined in claim 18 wherein said casting material is a die stone material.

21. Method as defined in claim 18 including using a modular base plate having an arcuate upright wall adjoining said planar upper surface and said arcuate wall adapted for adhesive connection to an articulator, said base plate further having an upper side and a lower side.

22. Method as defined in claim 21 including providing said base plate lower side with a configuration that is a mirror image of the upper side of said base plate with respect to said arcuate wall and planar surface.

23. Method as defined in claim 18 wherein said frictional engagement of said block downward projection will cause said downward projection to resiliently bow about a vertical axis through said downward projection.

24. Method as defined in claim 18 including engaging an upper part of said socket with an upper part of said downward projection to hold said block against rotation and lateral movement, and frictionally engaging a lower part of said socket with a lower part of said downward projection to hold said block against upward movement.

25. Method as defined in claim 18 wherein said blocks are generally rectangular.

*26. An apparatus for use in making a dental replica, comprising:*

*a base plate including an arcuate flange portion with a configuration commensurate with at least one quadrant of a person's dental structure, said flange portion having an upper surface;*

*a plurality of mounting blocks having a main body and an anchor tab projecting upwardly from said main body for attachment to said dental replica; and*

*means releasably attaching said mounting blocks to said upper surface of said arcuate flange portion.*

*27. An apparatus for use in making a dental replica, comprising:*

*a base plate including an arcuate flange portion with a configuration commensurate with at least one quadrant of a person's dental structure, said flange portion having an upper surface;*

*a plurality of mounting blocks having a main body and an anchor tab projecting upwardly from said main body for attachment to said dental replica; and*

*a connector releasably attaching said mounting blocks to said upper surface of said arcuate flange portion.*

*28. An apparatus as defined in claim 27, wherein said connector comprises:*

*a plurality of openings evenly spaced along said upper surface of said flange portion; and*

*a downwardly extending projection on said main body of each said mounting block, said projection fitting into a corresponding one of said openings to position said mounting blocks adjacent one another along said upper surface of said arcuate flange portion.*

*29. An apparatus as defined in claim 28, wherein each said downwardly extending projection is adapted to make an interference fit with said corresponding opening as said projection is fit within said opening.*

*30. An apparatus as defined in claim 28, wherein:*

*each said opening comprises a transverse rectangular slot extending through said arcuate flange portion; and*

*each said downwardly extending projection has a substantially rectangular cross-section and a lower end which extends through said rectangular slot, said lower end positioned substantially flush with a lower surface of said flange portion when said main body of each said mounting block contacts said upper surface of said flange portion.*

*31. An apparatus as defined in claim 30, wherein an upper end of each said downwardly extending projection includes a rectangular seat portion that is adapted to fit snugly within said rectangular slot when said main body of each said mounting block contacts said upper surface of said flange portion.*

*32. An apparatus as defined in claim 30, wherein each said downwardly extending projection includes a protuberance adjacent said lower end of said projection for making an interference fit with said rectangular slot as said projection is fit within said rectangular slot.*

*33. An apparatus as defined in claim 30, wherein said base plate further comprises an arcuate upright wall adjoining said arcuate flange portion and adapted for attachment to an articulator.*

*34. An apparatus as defined in claim 27, wherein said base plate further comprises an arcuate upright wall adjoining said arcuate flange portion for attachment to an articulator.*

*35. A method for making a dental replica with at least one cast replica segment that is selectively detachable and replaceable with respect to said dental replica, said method comprising the steps of:*

*filling a dental impression mold with uncured dental casting material;*

*inverting a base plate assembly, said assembly including a base plate having a configuration commensurate with at least one quadrant of a person's dental structure and a plurality of mounting blocks releasably attached to an upper surface of said base plate, said mounting blocks including an anchor tab projecting upwardly therefrom;*

*immersing said anchor tabs within said uncured casting material and allowing said casting material to harden and fixedly secure said mounting blocks to said hardened material;*

*removing said dental impression mold from said hardened material to provide a dental replica of hardened material mounted to and supported on said mounting blocks attached to said base plate; and*

*cutting vertically downwardly through said dental replica to at least one of said mounting blocks to provide a removable model segment comprising a selected tooth and gum replica mounted to at least one of said mounting blocks.*

*36. A method as described in claim 35, further including the step of smearing a quantity of said uncured casting material over said anchor tabs prior to immersing said anchor tabs in said uncured casting material.*

* * * * *